United States Patent
Oon et al.

(10) Patent No.: US 7,113,280 B2
(45) Date of Patent: Sep. 26, 2006

(54) DYE DETECTION METHOD AND APPARATUS

(75) Inventors: Chin Hin Oon, Penang (MY); King Wai Wong, Penang (MY); Kean Loo Keh, Penang (MY)

(73) Assignee: Avago Technologies ECBU IP (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 10/888,321

(22) Filed: Jul. 9, 2004

(65) Prior Publication Data

US 2006/0007444 A1    Jan. 12, 2006

(51) Int. Cl.
*G01J 3/50* (2006.01)

(52) U.S. Cl. ............... 356/406; 356/410; 68/12.27

(58) Field of Classification Search ............. 356/402, 356/405, 406, 407, 409, 410; 68/12.02, 12.27
See application file for complete search history.

(56) References Cited

U.S. PATENT DOCUMENTS

| | | | |
|---|---|---|---|
| 4,406,028 A | * | 9/1983 | Hazan et al. ............... 8/158 |
| 6,590,659 B1 | * | 7/2003 | Melnyk et al. ............. 356/406 |

* cited by examiner

*Primary Examiner*—F. L. Evans

(57) ABSTRACT

Method and apparatus for detecting the presence of a color dye in a water sample are described. Light is generated and passed through a water sample. A color sensor is utilized to measure the light that passes through the water sample. Based on the measured light, it is determined whether a dye color is present in the water sample.

18 Claims, 4 Drawing Sheets

DYE DETECTION METHOD AND APPARATUS

BACKGROUND OF THE INVENTION

Responding to consumer demand, modern washing machines offer users a host of different of options. This array of choices typically includes a first control for setting the temperature of the water (e.g., hot, warm or cold). For example, the temperature of both the wash cycle and the rinse cycle can be programmed. There is also a second control to set the length of wash and another control to select the type of wash cycle (e.g., light, heavy, or normal wash). Other washers allow a user to select a particular type of wash (e.g., a regular wash, a permanent press wash, and a delicates/hand washable wash) based on that type of clothes in the washer. With these increased options and settings, the possibility for user error (e.g., using an inappropriate water temperature or wash cycle for particular clothing) also increases.

There are also many cleaning products available in the marketplace. These cleaning products include detergents (e.g., detergents designed for color clothes, detergents designed to fight stains, detergents with bleach, etc.), bleach products, and fabric softeners. Furthermore, numerous spot removal products that are designed to pre-treat stains or other marks on clothing are also available. This array of products, while offering greater options, also increases the likelihood that a user may inappropriately mix, combine, or incorrectly apply these products due to a failure to follow directions, lack of expertise, carelessness, user mistake, or user error.

Concurrent with these trends in washing machine technology and cleaning product availability is the trend in the fashion industry to offer clothing with bright and vibrant colors. To meet consumer demand for bright, vibrant, and rich colors in clothing, clothing designers utilize different color dyes to achieve these color effects. These colors are often achieved by mixing several different colors and by including dark and rich dyes.

Since consumers are price conscious, another trend in the industry is for manufacturers to identify ways to reduce their costs. One way to reduce costs is to utilize less expensive dyes on the clothing. Unfortunately, fabrics with less expensive dyes may be more sensitive to the temperature of the wash and the type of wash cycle and not as color fast as a more expensive dye. For example, minor deviations from the ideal washing situation may cause the dye to run in the wash. Another way to reduce costs is for the manufacturer to skip the process of pre-washing the clothing that serves to wash out residual dyes or to pre-shrink the clothing. Unfortunately, an un-suspecting user washing an article of clothing for the first time may be disappointed to learn that 1) the clothing has shrunk and 2) the color dye in the article has run in the wash, possibly ruining other pieces of clothing in the wash.

The above factors and trends increase the likelihood of color dye run-off in the wash. The dye run off can stain white clothing or other lighter color clothing, thereby causing damage to many items of clothing if not all of the clothing in the wash. Based on the foregoing, there remains a need for a method and apparatus that can detect dye run-off in the wash before damage to the clothes occurs.

SUMMARY OF THE INVENTION

According to one embodiment of the present invention, a method and apparatus are described to detect the presence of a color dye in a water sample. Light is generated and passed through a water sample. A color sensor is utilized to measure the light that passes through the water sample. Based on the measured light, a dye detection mechanism is used to determine whether a dye color is present in the water sample.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

A dye detection method and apparatus are described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Washing Machine 100

Figure 1:
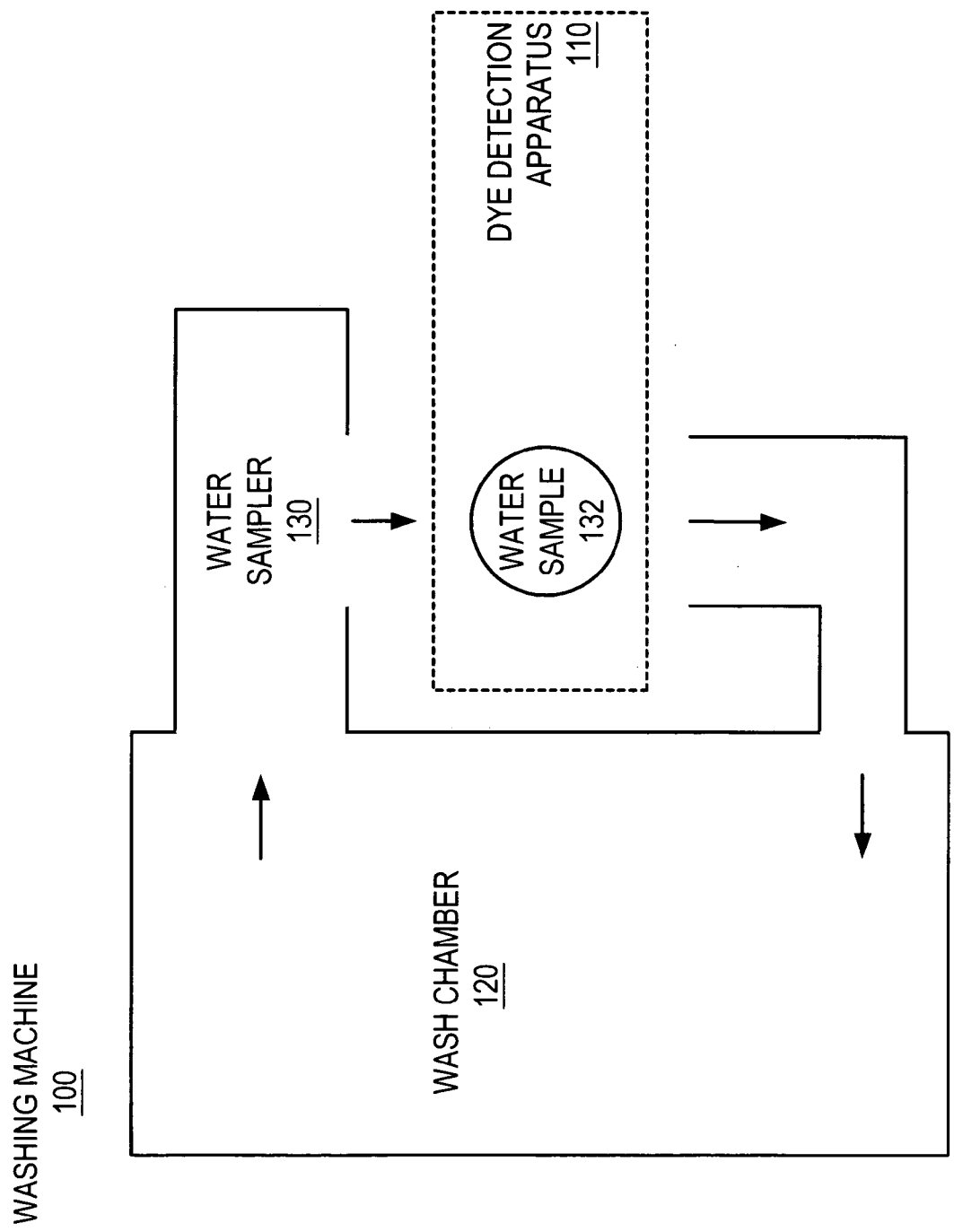
FIG. 1 illustrates a washing machine that includes the dye detection apparatus according to one embodiment of the invention.

FIG. 1 illustrates a washing machine 100 that includes a dye detection apparatus 110 according to one embodiment of the invention. The washing machine 100 includes a wash chamber 120 for holding the clothes to be washed and the water. The washing machine 100 also includes a water sampler 130 for diverting a sample of water (hereinafter referred to also as "water sample 132") from the wash chamber 120. The washing machine 100 also includes other components (not shown) whose construction and operation are known to those of ordinary skill in the art. These components can include, for example, a motor, drive belts, transmission, pump, hoses, agitator, control panel, control knobs and selectors.

The washing machine 100 also includes the dye detection apparatus 110 according to one embodiment of the invention for detecting whether the water sample 132 has dye present therein. In one embodiment, the water sample 132 is analyzed by the dye detection apparatus 110 as the water falls in free space. In another embodiment, the water sample 132 is diverted to a sampling conduit 140 that can be, for example, a transparent pipe through which the water sample 132 flows and then analyzed by the dye detection apparatus 110.

Initially, the water sample 132 from the wash chamber 120 includes relatively clear water with a predetermined transmittance corresponding to the clear water. For example, a baseline transmittance (e.g., a baseline ratio of the different color channels) that corresponds to the clean water may be stored or recorded by the dye detection apparatus 110 for future comparison with water than has detergent, water with dirt (e.g., dirty water), or water with dye color.

As the detergent is mixed with the water, the water sample 132 may become a murky white color. Also, as the clothes are being washed, the water sample 132 may become a dirtier color (e.g., a murky gray color) in addition to being murky white in color. As can be appreciated, this dirty and murky water has a transmittance that is lower than the baseline transmittance. In other words, as the transmittance of the water sample decreases, the amount of light from the light source that is detected by the color sensor is reduced. However, the color ratio remains the same for water with detergent and water with detergent and with dirt. When the color ratio changes, the dye detection mechanism according to the invention detects dye run-off.

As the wash progresses, the transmittance of the water sample 132 is periodically determined (e.g., a predetermined time interval). For example, the values at the color channels can be periodically measured, and based thereon a measured ratio of the color channels may be calculated. The measured ratio is then compared with the baseline ratio. When the measured ratio is different from the baseline ratio, it is determined that a dye-run off is occurring.

Once the dye detection apparatus 110 detects the presence of dye in the water sample 132, the dye detection apparatus 110 can alert a user by utilizing a visual alarm or an auditory alarm. The dye detection apparatus 110 can also utilize a predetermined procedure for mitigating or minimizing damage to clothes due to dye color run-off once such a run-off is detected. For example, the dye detection apparatus 110 can utilize the washing machine controller 150 to stop its current wash cycle and drain all water from the wash chamber 120 and perhaps initiate a spin cycle.

Dye Detection Apparatus with White LED as Light Source

Figure 2:
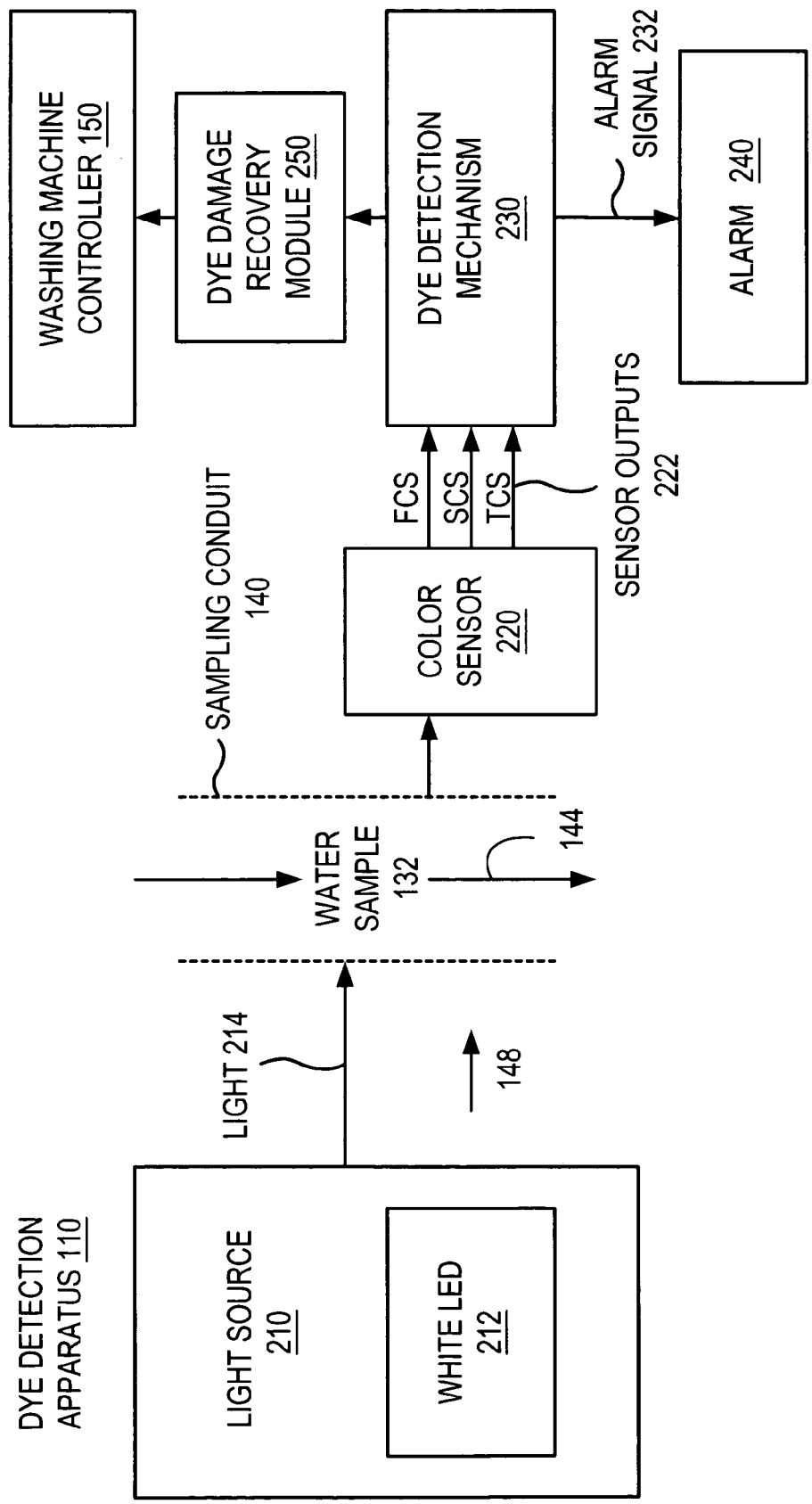
FIG. 2 illustrates a block diagram of the dye detection apparatus according to one embodiment of the invention.

FIG. 2 is a block diagram illustrating in greater detail the dye detection apparatus 110 of FIG. 1 according to one embodiment of the invention. The apparatus 110 detects the presence of a color dye in a water sample 132 and can be used in the washing machine 100 illustrated in FIG. 1.

The dye detection apparatus 110 includes a light source 210 for generating a light 214. In this embodiment, the light source 210 includes a white light emitting diode (LED) for generating a white light 214. The light source 210 is positioned with respect to the sampling conduit 140 so that the light 214 passes through the water sample 132 in a direction 148 that is generally perpendicular to the direction 144 of the flow of the water sample 132.

The apparatus 110 also includes a color sensor 220 that is positioned to receive the light that passes through the water sample 132. The color sensor 220 detects or measures the amount of light received from the light source 210 after the light has been optically filtered or changed by the water sample 132. In response to the measured light, the color sensor 220 generates one or more output signals 222 that represent the received light.

In one embodiment, the color sensor 220 includes a two color channels (RG, GB, or RB) and includes two output pins for generating two output signals, respectively: a first color signal (FCS) and a second color signal (SCS). The first color and second color can be, for example, the following combinations: (red color signal, green color signal), (red color signal, blue color signal), and (red color signal, green color signal).

In another embodiment, the color sensor 220 includes three color channels (R, G, B) and includes three output pins for generating three output signals, respectively: a first color signal (FCS) (e.g., a red signal output), a second color signal (SCS) (e.g., a green signal output), and a third color signal (TCS) (e.g., a blue signal output). The color signal can be in the form of a voltage, current, or other signal format.

It is noted that the color sensor 220 can have more than three-color channels. Also, it is noted that the color channels are not limited to a red, green and blue channels and may include other colors such as cyan, magenta, and yellow.

The apparatus 110 also includes a dye detection mechanism 230 that is coupled to the color sensor 220 for receiving the output signal 222 of the color sensor, and based thereon determines whether a dye color is present in the water sample 132. The apparatus 110 also includes an alarm 240. When the dye detection mechanism 230 determines that dye color is present in the water sample 132, the dye detection activates the alarm 240. The dye detection mechanism 230 can activate the alarm 240, for example, by asserting an alarm signal 232. The alarm 240 can provide a user with an audible cue or a visual cue to alert the user that dye run-off has occurred in the wash (e.g., color dye is present in the wash).

The apparatus 110 also includes a dye damage recovery module 250. When the dye detection mechanism 230 determines that dye color is present in the water sample 132, the dye detection mechanism 230 can also activate the dye damage recovery module 250 by asserting one or more signals and providing these signals to the dye damage recovery module 250. The dye damage recovery module 250 generates and sends one or more signals to the washing machine controller 150. These signals can notify the washing machine controller 150 that dye is present. These signals can also control the washing machine controller 150 to take remedial measures, such as turning off the wash cycle, draining the water from the wash chamber 120, etc.

The dye detection apparatus 110 can be implemented, for example, in a household washing machine, a commercial washing machine, or a dry cleaning washing machine.

Dye Detection Apparatus with Tri-color LED as Light Source

Figure 3:
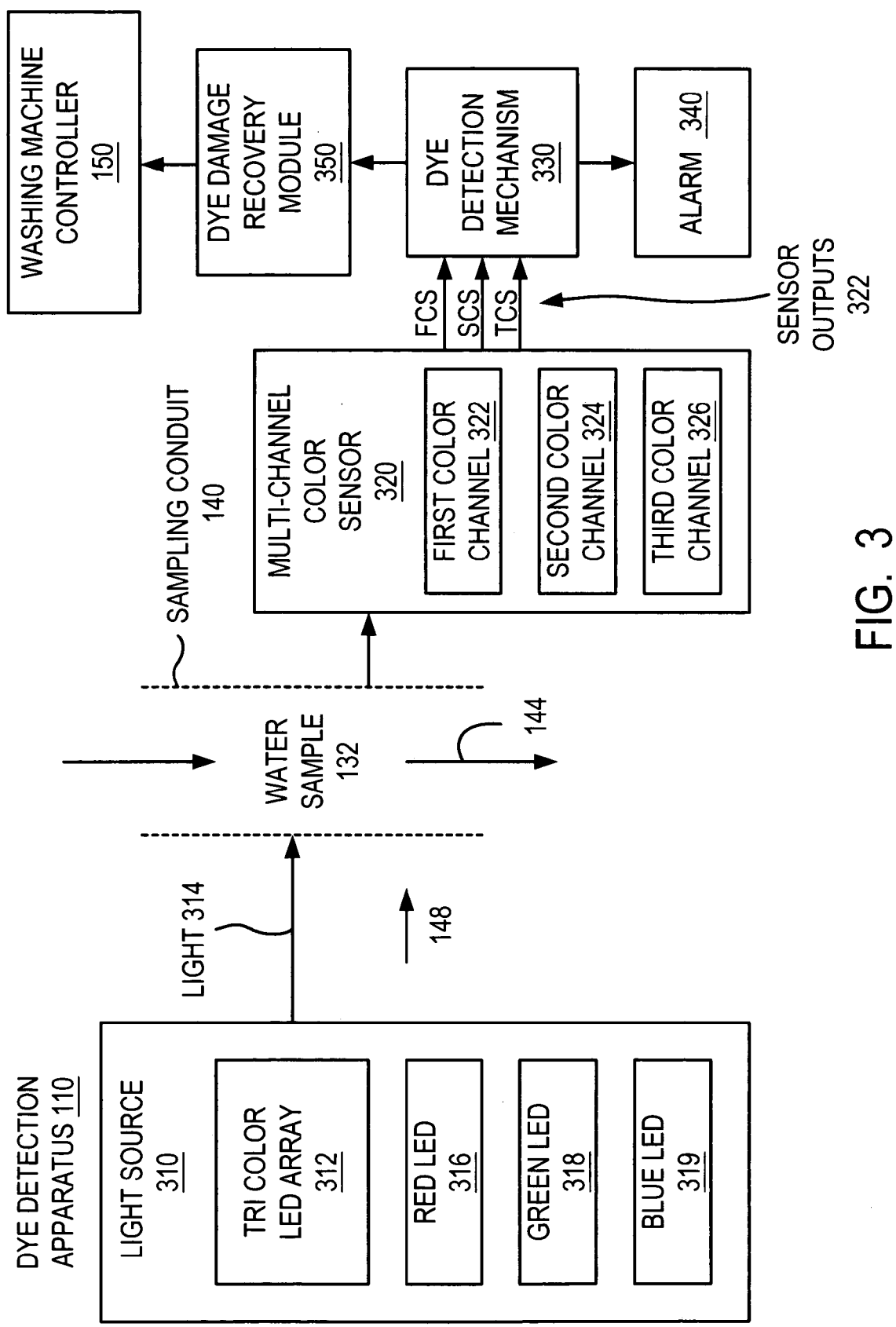
FIG. 3 illustrates a block diagram of the dye detection apparatus according to another embodiment of the invention.

FIG. 3 is a block diagram illustrating in greater detail the dye detection apparatus 110 of FIG. 1 according to another embodiment of the invention. The apparatus 110 detects the presence of a color dye in a water sample and can be used in a washing machine as illustrated in FIG. 1.

The dye detection apparatus 110 includes a light source 310 for generating a light 314. In this embodiment, the light source 310 can includes a tri-color light emitting diode (LED) array 312. The tri-color light emitting diode (LED) array includes a red light emitting diode (LED) 316 for generating a red light, a green light emitting diode (LED) 318 for generating a green light, and a blue light emitting diode (LED) 319 for generating a blue light.

The light 314 includes a red component, green component and a blue component that is generated by the red light emitting diode (LED) 316, the green light emitting diode (LED) 318, and a blue light emitting diode (LED) 319, respectively.

The light source 310 is positioned so that the generated light 314 passes through the water sample 132 in a direction 148 that is generally perpendicular to the direction 144 of the flow of the water sample 132. When a sampling conduit 140 is utilized, the light source 310 can be positioned with respect to the sampling conduit 140 so that the generated light 314 passes through the water sample 132 in a direction 148 that is generally perpendicular to the direction 144 of the flow of the water sample 132.

The apparatus 110 also includes a color sensor 320 that is positioned to detect the light that passes through the water sample 132. The color sensor 320 detects or measures the amount of light received from the light source 310 after the light has been optically filtered or changed by the water sample 132. In response to the measured light, the color sensor 320 generates an output signal 322 that is representative of the received light.

In one embodiment, the color sensor 320 is implemented with a multi-channel color sensor that includes a plurality of color channels (e.g., 322, 324, 326). Unlike typical sensors that detect only one color, the color sensor 320 can detect three colors (e.g., red, green, and blue). In this regard, the color sensor 320 includes a first output for generating a first color signal (FCS) (e.g., a red color signal), a second output for generating a second color signal (SCS) (e.g., a green color signal), and a third output for generating a third color signal (TCS) (e.g., a blue color signal). In this example, the color sensor 320 includes three color channels: 1) a red color channel 322, 2) a green color channel 324, and 3) a blue color channel 326.

The apparatus 110 also includes a dye detection mechanism 330 that is coupled to the color sensor 320 for receiving the output signals of the color sensor, determining whether a dye color is present in the water sample, and if so, generating an alarm signal. The alarm signal is provided to activate the alarm 240. For example, the alarm 240 can be utilized to provide a user with an audible or visual cue that color dye is present in the washing machine.

Dye Detection Processing

Figure 4:
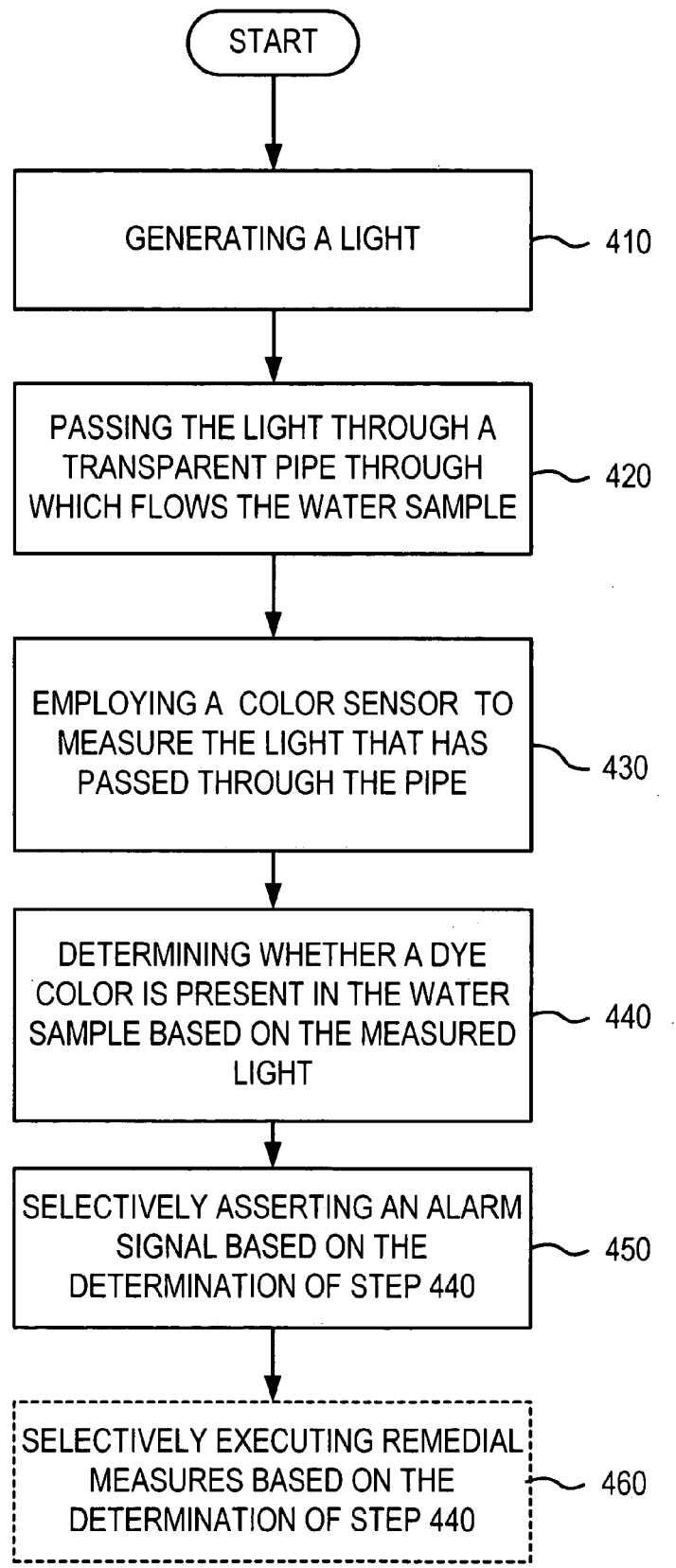
FIG. 4 is a flow chart illustrating the processing steps performed by the dye detection apparatus according to one embodiment of the invention.

FIG. 4 is a flow chart illustrating the processing steps performed by the dye detection apparatus 110 according to one embodiment of the invention. A method for detecting the presence of a color dye in a water sample according to the invention is now described. In step 410, a light is generated. This light can be a white light generated by a white light emitting diode (LED) or a tri-colored light generated by a red/green/blue light emitting diode (LED). In step 420, the generated light is passed through a transparent pipe through which flows the water sample. For example, the light can be directed or focused to shine incident to one side of the pipe. In step 430, the light that passes through the pipe is measured. For example, color sensor 320 may be employed to make this light measurement. In step 440, it is selectively determined based on the received light whether a dye color is present in the water sample.

For example, when clear and clean water, the voltage on the red channel, the voltage on the green channel, and the voltage on the blue channel are as follows: 1V:1V:1V. The baseline ratio between the color channels is calculated to be 1:1:1. However, when the water becomes murky from soap/dirt etc., the voltages of the three channels (R, G, B) may decrease, for example, to 0.5V:0.5V:0.5V. However, the measured ratio between the color channels is the same as the baseline ratio and remains 1:1:1.

Murky water, dirty water, or brackish water, tends to attenuate the light from various wavelengths evenly. For example, murky water attenuates the voltage of the three channels (R, G, B) from 1V:1V:1V (clear water) to 0.5V: 0.5V:0.5V. However, when a blue dye is present in the water, the bluish water attenuates the red channel and green channel more than the blue channel, thereby changing the measured ratio. Consequently, the measured ratio between the different color channels would not remain equal or the same as the baseline ratio in this case.

When dye from clothes starts to run, the measured ratio itself changes and becomes, for example, 0.6:0.4:0.3. In other words, although the absolute voltage in each channel may decrease due to murky or cloudy water, the measured ratio of the different channels to each other remains the same as the baseline ratio. However, when dye begins to run, the measured ratio between the color channels changes or differs from the baseline ratio. In one embodiment, the dye detection mechanism according to the invention detects this change in the measured ratio between the color channels.

The dye detection mechanism according to the invention utilizes the color sensor with multiple color channels to determine whether the measured ratio between the various color channels remains the same as the baseline ratio or changes from the baseline ratio. When the measured ratio changes or diverges from the baseline ratio, dye run-off has been detected in the water. In this manner, the photo sensor with multiple color channels according to the invention can be employed to differentiate between brackish water and dyed water. It is noted that a typical photo sensor that only has a color single channel cannot differentiate between the two cases: 1) water with dye and 2) murky water or brackish water. Such a sensor detects a reduction in the light, but cannot differentiate between light that is passed through brackish water or light that is passed through water with dye run-off.

In another embodiment, the dye detection mechanism according to the invention increases performance by the following technique. When the water becomes murky, the brightness of the light source (e.g., LED) is increased until the output of one of the color channels reaches a previous voltage level (e.g., a predetermined voltage level of 1V). When the water is brackish or murky, then all the color channels reach the following voltage levels at about the same time: 1V:1V:1V. However, when there is dye in the water, one voltages of the color channels reaches 1V before the voltages of the other channels reach the predetermined previous level (e.g., 0.6V:0.7V:1.0V).

In step 450, when it is determined that a dye color is present in the water sample, an alarm is generated to notify a user to take measures that prevent further damage to the items being washed. For example, the alarm can be an audible or visual alarm. The user can stop the washing machine and remove the article or item that is causing the color dye run-off or perform other actions to prevent further damage to the items being washed.

In step 460, when it is determined that a dye color is present in the water sample, remedial steps are optionally executed. These remedial measures can include any steps that would reverse the damage to the clothes caused by the dye or stop further damage to the clothes. For example, the remedial measures can include instructing the washing machine to stop the wash cycle, drain the water, initiate a spin cycle, etc.

In the foregoing specification, the invention has been described with reference to specific embodiments thereof. It will, however, be evident that various modifications and changes may be made thereto without departing from the broader scope of the invention. The specification and drawings are, accordingly, to be regarded in an illustrative rather than a restrictive sense.

What is claimed is:

1. An apparatus for detecting the presence of a color dye in a water sample, comprising:

a) a light source to generate a light that passes through the water sample;

b) a color sensor that includes a first color output and a second color output to measure the light that has passed through the water sample by generating at least a first color signal and a second color signal based on the received light; and c) a dye detection mechanism coupled to the color sensor to receive the color signals and to determine whether the dye color is present in the water sample based on the color signals; wherein the dye detection mechanism during a wash periodically determines a measured ratio between the first color signal and the second color signal, compares the measured ratio with a baseline ratio, and determines that dye color is present in the water sample when the measured ratio changes from the baseline ratio.

2. The apparatus of claim 1 wherein the dye detection mechanism initially determines the baseline ratio between the first color signal and the second color signal based on one of clear water, water with detergent, and dirty water with detergent and stores the baseline ratio.

3. The apparatus of claim 1 wherein the color sensor includes a first color channel, a second color channel, and a third color channel; wherein the first color is red, the second color is green, and the third color is blue; wherein the color sensor further generates a third color signal; and wherein the dye detection mechanism during the wash periodically determines a measured ratio that includes at least one of a first measured ratio between the first color signal and the second color signal, a second measured ratio between the second color signal and the third color signal, and a third measured ratio between the first color signal and the third color signal, compares the measured ratio with a baseline ratio that includes at least one of a first baseline ratio between the first color signal and the second color signal, a second baseline ratio between the second color signal and the third color signal, and a third baseline ratio between the first color signal and the third color signal, and determines that dye color is present in the water sample when the measured ratio changes from the baseline ratio.

4. The apparatus of claim 3 wherein the dye detection mechanism initially determines the baseline ratio based on one of clear water, water with detergent and dirty water with detergent and stores the baseline ratio.

5. The apparatus of claim 1 wherein the light source is one of a white light emitting diode (LED) and a tri-color light emitting diode (LED) array.

6. The apparatus of claim 5 wherein the tri-color light emitting diode (LED) array includes a red light emitting diode (LED), a green light emitting diode (LED), and a blue light emitting diode (LED); and wherein the color sensor includes a red color signal output, a green color signal output, and a blue color signal output.

7. The apparatus of claim 1 wherein the apparatus is implemented in a washing machine that includes a plurality of operations; where the apparatus further comprises:

a dye damage recovery mechanism to adjust at least one operation of the washing machine when dye color has been detected in the water sample to one of prevent further dye damage and reduce current dye damage.

8. The apparatus of claim 7, wherein the dye damage recovery mechanism performs one of stopping the current wash cycle, draining water from the wash chamber, and spin-drying the current wash load.

9. The apparatus of claim 1 further comprising:

an alarm to receive an alarm signal and based thereon to provide one of a visual alert and an audible alert to notify a user of dye run-off;

wherein the dye detection mechanism selectively asserts the alarm signal when dye run-off has been detected.

10. The apparatus of claim 1, further comprising a sampling conduit through which the water sample flows in a first direction; wherein the light source is positioned with respect to the sampling conduit to pass light through the sampling conduit in a second direction that is generally perpendicular to the first direction.

11. A washing machine, comprising:

a wash chamber; and a color dye detection system used to detect the presence of a color dye in a water sample collected from the wash chamber, further comprising:

a) a light source to generate a light that passes through the water sample;

b) a color sensor to measure the light that has passed through the water sample by generating at least a first color signal and second color signal based on the received light; and c) a dye detection mechanism coupled to the color sensor to receive the color signals and to determine whether the dye color is present in the water sample based on the color signals; wherein the dye detection mechanism during the wash periodically determines a measured ratio between the first color signal and the second color signal, compares the measured ratio with a baseline ratio, and determines that dye color is present in the water sample when the measured ratio changes from the baseline ratio.

12. The washing machine of claim 11 wherein the dye detection mechanism initially determines the baseline ratio between the first color signal and the second color signal based on one of clear water, water with detergent, and dirty water with detergent and stores the baseline ratio.

13. The washing machine of claim 11 wherein the color sensor includes a first color channel, a second color channel, and a third color channel; wherein the first color is red, the second color is green, and the third color is blue; wherein the color sensor futher generates a third color signal; and wherein the dye detection mechanism during a wash periodically determines a measured ratio that includes at least one of a first measured ratio between the first color signal and the second color signal, a second measured ratio between the second color signal and the third color signal, and a third measured ratio between the first color signal and the third color signal, compares the measured ratio with a baseline ratio that includes at least one of a first baseline ratio between the first color signal and the second color signal, a second baseline ratio between the second color signal and the third color signal, and a third baseline ratio between the first color signal and the third color signal, and determines that dye color is present in the water sample when the measured ratio changes from the baseline ratio.

14. The washing machine of claim 13 wherein the dye detection mechanism initially determines the baseline ratio based on one of clear water, water with detergent, and dirty water with detergent and stores the baseline ratio.

15. The washing machine of claim 11 wherein the light source is one of a white light emitting diode (LED), a tri-color light emitting diode (LED) array, a light emitting diode (LED) array that includes a red light emitting diode (LED), a green light emitting diode (LED), and a blue light emitting diode (LED); and wherein the color sensor includes a red color signal output, a green color signal output, and a blue color signal output.

16. The apparatus of claim 11 further comprising:
a dye damage recovery mechanism for adjusting at least one operation of the washing machine when dye color has been detected in the washing machine to one of preventing further dye damage and reducing current dye damage.

17. A method for detecting the presence of a color dye in a water sample comprising:
a) generating a light that passes through the water sample;
b) employing a color sensor to measure the light that has passed through the water sample; and
c) determining whether a dye color is present in the water sample based on the measured light; wherein determining whether a dye color is present in the water sample based on the measured light includes during the wash periodically determining a measured ratio between the first color signal and the second color signal, comparing the measured ratio with a baseline ratio, and determining that dye color is present in the water sample when the measured ratio changes from the baseline ratio.

18. The method of claim 17 wherein employing a color sensor to measure the light that has passed through the water sample includes
generating a first color signal, a second color signal, and a third color signal; and
wherein determining whether a dye color is present in the water sample based on the measured light includes
periodically determining during the wash a measured ratio that includes at least one of a first measured ratio between the first color signal and the second color signal, a second measured ratio between the second color signal and the third color signal, and a third measured ratio between the first color signal and the third color signal;
comparing the measured ratio with a baseline ratio that includes at least one of a first baseline ratio between the first color signal and the second color signal, a second baseline ratio between the second color signal and the third color signal, and a third baseline ratio between the first color signal and the third color signal; and
determining that dye color is present in the water sample when the measured ratio changes from the baseline ratio.

* * * * *